US009453055B2

(12) United States Patent
Komiya et al.

(10) Patent No.: US 9,453,055 B2
(45) Date of Patent: Sep. 27, 2016

(54) METHOD OF PRODUCING JAPANESE ENCEPHALITIS VACCINE STABLY STORABLE OVER LONG TIME AND USE OF THE VACCINE

(75) Inventors: Tomoyoshi Komiya, Saitama (JP); Hiroko Toriniwa, Saitama (JP)

(73) Assignee: Kitasato Daiichi Sankyo Vaccine Co., Ltd., Tokyo (JP)

( * ) Notice: Subject to any disclaimer, the term of this patent is extended or adjusted under 35 U.S.C. 154(b) by 387 days.

(21) Appl. No.: 12/810,447

(22) PCT Filed: Dec. 26, 2008

(86) PCT No.: PCT/JP2008/073732
§ 371 (c)(1),
(2), (4) Date: Sep. 17, 2010

(87) PCT Pub. No.: WO2009/082002
PCT Pub. Date: Jul. 2, 2009

(65) Prior Publication Data
US 2011/0020393 A1  Jan. 27, 2011

(30) Foreign Application Priority Data
Dec. 26, 2007 (JP) ................. 2007-334909

(51) Int. Cl.
C12N 7/04 (2006.01)
A61K 39/12 (2006.01)
C07K 14/005 (2006.01)
A61K 39/00 (2006.01)

(52) U.S. Cl.
CPC ............ *C07K 14/005* (2013.01); *A61K 39/12* (2013.01); *A61K 39/00* (2013.01); *A61K 2039/5252* (2013.01); *C12N 2770/24122* (2013.01); *C12N 2770/24134* (2013.01)

(58) Field of Classification Search
CPC .............. A61K 2039/5252; A61K 39/12; A61K 39/00; C12N 2770/24134; C12N 2770/24122; C07K 14/005
See application file for complete search history.

(56) References Cited

U.S. PATENT DOCUMENTS

| | | | |
|---|---|---|---|
| 5,891,705 A | 4/1999 | Budowsky et al. | |
| 6,149,917 A | 11/2000 | Fanget et al. | |
| 6,309,650 B1 | 10/2001 | Kim et al. | |
| 6,841,374 B1 | 1/2005 | Ishikawa et al. | |

FOREIGN PATENT DOCUMENTS

| | | |
|---|---|---|
| CA | 2 390 995 A1 | 5/2001 |
| CN | 1272879 | 11/2000 |
| EP | 0878541 | 11/1998 |
| EP | 1604685 | 12/2005 |
| IN | 216099 | 12/2005 |
| JP | 31009498 | 11/1956 |
| JP | 42-006817 | 3/1967 |
| JP | 49020322 | 2/1974 |
| JP | 200083657 | 3/2000 |
| JP | 2001514844 | 9/2001 |
| KR | 10-1999-0023955 | 3/1999 |
| KR | 10-1999-0072201 | 9/1999 |
| WO | WO 97/04803 A1 | 2/1997 |
| WO | WO 99/11762 A1 | 3/1999 |
| WO | 0176624 A1 | 10/2001 |

OTHER PUBLICATIONS

Database WPI, Accession No. 1966-26048F, Abstract for JP 1967-006817 B, Thomson Scientific, London, accessed Feb. 22, 2012.
Supplementary European Search Report for European Patent Appl. No. EP 08 86 4833, completed Nov. 22, 2011, European Patent Office, The Hague, The Netherland.
Toriniwa, H. and Komiya, T., "Long-term stability of Vero cell-derived inactivated Japanese encephalitis vaccine prepared using seru-free medium, " *Vaccine* 26:3680-3689, Elsevier Ltd. (2008).
Barteling, S.J. & Woortmeyer, R., "Formaldehyde Inactivation of Foot-and-Mouth Disease Virus. Conditions for the Preparation of Safe Vaccine," *Archives of Virology* 80:103-117, Springer-Verlag, Germany (1984).
Lyons, A., et al., "A Phase 2 study of a purified, inactivated virus vaccine to prevent Japanese encephalitis," *Vaccine* 25:3445-3453, Elsevier Ltd., United Kingdom (2007).
Marquie, C., et al., "How to monitor the protein cross-linking by formaldehyde, glutaraldehyde or glyoxal in cotton-seed protein-based films?," *Nahrung* 42:264-265, Wiley-VCH GmbH, Germany (1998).
McClurg, W.M., et al., "Formaldehyde Replaces Glutaraldehyde in Porcine. Bioprosthetic Heart Valves," *The Journal of Heart Valve Disease* 5:343-347, ICR Publishers, United Kingdom (1996).
Metz, B., et al., "Identification of Formaldehyde-induced Modifications in Proteins,". *The Journal of Biological Chemistry* 279:6235-6243, The American Society for Biochemistry and Molecuar Biology, Inc., United States (2004)
Srivastava, A.K., et al., "A purified inactivated Japanese encephalitis virus vaccine made in vero cells," *Vaccine* 19:4557-4565, Elsevier Science Ltd., United Kingdom (2001).
Sugawara, K., et al., "Development of Vero Cell-Derived Inactivated Japanese Encephalitis Vaccine," *Biologicals* 30:303-314, Elsevier Science Ltd., United Kingdom (2002).

(Continued)

*Primary Examiner* — Stacy B Chen
(74) *Attorney, Agent, or Firm* — Andrus Intellectual Property Law, LLP

(57) ABSTRACT

The present inventors improved methods for inactivating Japanese encephalitis virus vaccines, and assessed the safety of vaccines produced by combining multiple vaccines. The present inventors successfully produced safer Japanese encephalitis vaccines by cell culture, which can be stored more stably over a long period than conventional Japanese encephalitis vaccines. Furthermore, it is also expected that the production methods can be used to produce other viral vaccines with excellent storage stability.

10 Claims, No Drawings

(56) References Cited

OTHER PUBLICATIONS

Tsai, T.F., et al., "Chapter 27: Japanese Encephalitis Vaccines," in Vaccines, 3rd edition, pp. 672-710 (Plotkin, S.A. and Orenstein, W.A. ed., 1999)

Wu, S.-C. & Huang, G.Y.-L., "Stationary and Microcarrier Cell Culture Processes for Propagating Japanese Encephalitis Virus," *Biotechnol. Prog.* 18:124-128, American Chemical Society and American Institute of Chemical Engineers, United States (2002).

International Search Report for International Application No. PCT/JP2008/073732,.Japanese Patent Office, Japan, mailed on Feb. 3, 2009.

Komiya et al., "Soshiki Baiyo Yurai Fukatsuka Nihonnoen Vaccine no Anteisei ni Tsuite", Gakujutsu Shukai Program Shoroku-shu, 2006, 54:252—English Translation, "The Stability of Inactivated Japanese Encephalitis Vaccine Derived from Tissue Culture".

Appaiahgari et al., "Immunogenicity and protective efficacy in mice of a formaldehyde-inactivated Indian strain of Japanese encephalitis virus grown in Vero cells", Vaccine, 2004, 22:3669-3675.

Singh et al., "The osmoprotectancts glycine and its methyl derivatives prevent the thermal inactivation of protective antigen of Bacillus anthracis", Biochemical and Biophysical Research Communication, 2004, 316:559-564.

"Regulations for Japanese Encephalitis (Inactivated) Vaccine for Human Use", Regulations for Biological Preparations, Oct. 1, 1989, 43.

De Rizzo et al., "Sorbitol-gelatin and glutamic acid-lactose solutions for stabilization of reference preparations of measles virus," Bull Pan Am Health Organ. 1989; 23(3)299-305.

METHOD OF PRODUCING JAPANESE ENCEPHALITIS VACCINE STABLY STORABLE OVER LONG TIME AND USE OF THE VACCINE

TECHNICAL FIELD

The present invention relates to methods for producing Japanese encephalitis vaccines characterized by the substantial maintenance of their titers even over long-term storage. The present invention also relates to Japanese encephalitis vaccines produced by the methods of the present invention, and combination vaccines comprising Japanese encephalitis vaccines and other types of antigen vaccines. Furthermore, the present invention relates to methods for preventing a disease caused by a bacterium and/or virus in a subject, which comprise the step of administering a vaccine of the present invention to the subject.

BACKGROUND ART

Japanese encephalitis is an infectious disease caused by infection with the Japanese encephalitis virus which is transmitted by mosquitoes such as *Culex tritaeniorhyncus*. The infection can occur even early after birth. The viral infection causes encephalopathy, leading to severe sequelae and high mortality rate. The immunity conferred by vaccination from early infancy is effective to prevent the disease. The Japanese encephalitis virus belongs to Flaviviridae. Vaccines used for preventing Japanese encephalitis have been produced and are commercially available. Japanese encephalitis vaccination is included in the routine vaccination in Japan. Based on the type of production method, Japanese encephalitis vaccines are categorized into vaccines produced by the mouse brain method and vaccines produced by the cell culture method. Also, there are inactivated Japanese encephalitis vaccines and attenuated live Japanese encephalitis vaccines. As for the dosage form, liquid vaccines and lyophilized vaccines have been produced and are commercially available. The theory of inactivated Japanese encephalitis vaccines produced by the mouse brain method is briefly described below.

The first Japanese encephalitis vaccine, which was a mouse brain-derived vaccine, was put to practical use in 1954. However, it was pointed out that the purity was low and there was a risk of vaccine inducing allergic central nervous system disorders. Subsequently, constant improvements were made to further purify the virus. An improved Japanese encephalitis vaccine with higher quality was put to practical use in 1965. The production techniques have been used up to the present date.

As mentioned above, inactivated Japanese encephalitis vaccines produced by the mouse brain method are highly pure and effective. However, it has been pointed out that the inactivated Japanese encephalitis vaccines have problems in safety and storage stability.

In view of the presently required safety level, there is a safety problem that because the vaccines are produced using mice housed in an insufficiently controlled environment, the possibility of adventitious agents being contaminated in vaccine products cannot be ruled out. Basically, this problem can be solved by using the cell culture-based production method. Recently, vaccines produced by the cell culture method have drawn attention all over the world, and there is a worldwide demand for vaccines in both advanced and developing countries. To solve the storage stability problem, gelatin has been added to vaccines as a stabilizer. However, it was pointed out that gelatin has the risk of inducing allergic reactions, and has become less frequent as a stabilizer. An alternative method to secure storage stability is to manufacture lyophilized products, and they can be stored for a long period in a cold room. However, the production cost of lyophilized products is high. Also, lyophilized products have the disadvantage of high storage cost, since cold-room or frozen storage requires storage facilities and devices such as refrigerators.

In conclusion, the efficacy, safety, and storage stability of inactivated Japanese encephalitis vaccines are summarized as follows. The efficacy is relatively satisfactory. The safety problem can be solved by developing a cell culture-based production method. The storage stability problem may be solved by using the lyophilization method; however, this method has the disadvantage of high production cost, while the storage stability of liquid products is not secured. That is, there is a demand for a new Japanese encephalitis vaccine that can be stored stably for a long period.

For another reason, improvement of the storage stability of liquid products is needed. Liquid products are usually inoculated by injection. In areas without sufficient medical facilities or specialists, there is a demand for supply of stable liquid Japanese encephalitis vaccine products that are used for transnasal or transdermal inoculation.

There is a need to develop not only Japanese encephalitis vaccines but also other viral vaccines that are excellent in the storage stability while maintaining low production costs.

Prior art documents related to the present invention include:

[Patent Document 1] CA 2,390,995
[Patent Document 2] U.S. Pat. No. 6,841,374
[Patent Document 3] EP 841,942
[Patent Document 4] U.S. Pat. No. 5,891,705
[Non-Patent Document 1] T F Tsai et al (1999): In, Vaccines (3 rd Ed.) (ed. by S A Plotkin and W A Orenstein, 1999), pp 672-710: Japanese Encephaitis vaccine.
[Non-Patent Document 2] K Sugawara et al (2002): Biologicals, 30, 303-314: Development of Vero cell-derived Inactivated Japanese Encephalitis vaccine.
[Non-Patent Document 3] S C Wu, G Y-L Huang (2002): Biotechnol. Prog. 18, 124-128: Stationary and microcarrier cell culture processes for propagating Japanese Encephalitis virus.
[Non-Patent Document 4] A K Srivastava et al (2001): Vaccine 19, 4557-75: A purified inactivated Japanese Encephalitis vaccine made in vero cells.
[Non-Patent Document 5] A Lyons et al. (2007): Vaccine 25, 3445-53: A phase 2 study of a purified inactivated virus vaccine to prevent Japanese Encephalitis.
[Non-Patent Document 6] S J Barteling, R. Woortmeyer (1984): Arch Virol. 80(2-3), 103-17: Formaldehyde inactivation of foot-and-mouth disease virus: Conditions for the preparation of safe vaccine.
[Non-Patent Document 7] B Metz et al. (2004): J. Biol. Chem., 279 (8), 6235-6243: Identification of Formaldehyde-induced Modifications in Proteins: reactions with model peptides.
[Non-Patent Document 8] C Marquie et al. (1998): Nahrung/Food (3/4), 42, 264-265: How to monitor the protein cross-linking by formaldehyde, glutaraldehyde or glyoxal in cotton-seed protein protein-based films? (short communication)
[Non-Patent Document 9] W M McClurg et al. (1996): J Heart Valve Dis. 5(3), 343-7: Formaldehyde replaces glutaraldehyde in porcine bioprosthetic heart valves.

DISCLOSURE OF THE INVENTION

Problems to be Solved by the Invention

The present invention was achieved in view of the above circumstances. An objective of the present invention is to solve the problems of inactivated Japanese encephalitis vaccines produced by the mouse brain method. More specifically, an objective of the present invention is to provide methods for producing effective and safe inactivated liquid Japanese encephalitis vaccines that can be stored for a long period even around room temperature, which comprises the step of combining multiple inactivation treatments for Japanese encephalitis viruses obtained by the cell culture method. Another objective of the present invention is to provide Japanese encephalitis vaccines produced by the above production methods, as well as combination vaccines obtained by combining the stable Japanese encephalitis vaccines with other types of antigen vaccines. Another objective of the present invention is to provide methods of using the vaccines.

Means for Solving the Problems

To achieve the above objectives, the present inventors investigated methods for inactivating Japanese encephalitis viruses obtained by the cell culture method. The present inventors also assessed the storage stability of combination vaccines produced by combining multiple vaccines.

First, the present inventors investigated treatment conditions for inactivating Japanese encephalitis viruses. It was discovered that inactivated liquid Japanese encephalitis vaccines storable for a long period (for example, two years (24 months) or more) around room temperature can be produced by carrying out inactivation treatment in the presence of an amino acid or the like. Furthermore, the present inventors found that inactivated liquid Japanese encephalitis vaccines storable for a long period around room temperature can also be produced by including the step of carrying out additional physicochemical treatments for inactivation performed in the presence of an amino acid or the like, the step of carrying out formalin, heat-mediated inactivation, or such. Then, the present inventors combined an inactivated liquid Japanese encephalitis vaccine with improved storage stability prepared by the above methods with other vaccines, and assessed the resulting combination vaccine. The result demonstrated that the Japanese encephalitis vaccine can be stored stably for a long period even in the combination vaccine. Furthermore, it was revealed that the stability of Japanese encephalitis vaccines is retained by adding a stabilizer such as an amino acid after purification, in addition to the amino acid addition at the time of inactivation.

That is, by combining the multiple inactivation treatment step, the present inventors successfully produced low-cost Japanese encephalitis vaccines with both improved safety and storage stability as compared to inactivated Japanese encephalitis vaccines produced by the conventional mouse brain method, and thereby completed the present invention.

More specifically, the present invention provides [1] to [20] below:

[1] a method for producing an inactivated whole Japanese encephalitis vaccine, which comprises the step(s) of:
(a) carrying out an inactivation treatment for a Japanese encephalitis virus by a chemical technique in the presence of an amino acid, amine, amide, and/or organic acid; and/or
(b) carrying out an inactivation treatment for a Japanese encephalitis virus by a physicochemical technique;

[2] the method for producing a Japanese encephalitis vaccine of [1], wherein the amino acid in (a) of [1] is at least an amino acid selected from aspartic acid, γ-aminobutyric acid, alanine, β-alanine, arginine, glycine, glutamic acid, isoleucine, leucine, lysine, serine, threonine, and valine;

[3] the method for producing a Japanese encephalitis vaccine of [1] or [2], wherein the amine in (a) of [1] is at least an amine selected from ethylamine, ethanolamine, and propanolamine; the amide in (a) of [1] is at least an amide selected from urea, glycineamide, and β-alanylamide; or the organic acid in (a) of [1] is at least an organic acid selected from succinic acid, tartaric acid, gluconic acid, oleic acid, and lactobionic acid;

[4] the method for producing a Japanese encephalitis vaccine of any one of [1] to [3], wherein the inactivation treatment in (b) of Ellis at least a treatment method selected from heating, γ-ray irradiation, electron beam irradiation, and laser irradiation;

[5] the method for producing a Japanese encephalitis vaccine of [4], wherein the inactivation treatment by heating is carried out at 24° C. or higher;

[6] the method for producing a Japanese encephalitis vaccine of any one of [1] to [5], wherein the Japanese encephalitis virus is any one of a clinically isolated strain (wild type stain), an artificial mutant strain, a genetic recombinant strain, and a strain engineered by reverse genetics;

[7] the method for producing a Japanese encephalitis vaccine of any one of [1] to [6], which uses a Japanese encephalitis virus produced by the cell culture method;

[8] the method for producing a Japanese encephalitis vaccine of any one of [1] to [6], which uses a Japanese encephalitis virus produced by the serum-free culture method;

[9] the method for producing a Japanese encephalitis vaccine of [7] or [8], wherein a master cell bank produced by the serum-free culture method is used as a seed for cell culture;

[10] an inactivated whole Japanese encephalitis vaccine produced by the production method of any one of [1] to [9], which can retain its titer in long-term storage;

[11] the Japanese encephalitis vaccine of [10], which can retain its titer in long-term storage at a temperature between 15° C. and 40° C.;

[12] the Japanese encephalitis vaccine of [10], which comprises an amino acid, amine, and/or amide as a stabilizer;

[13] the Japanese encephalitis vaccine of [10], which is stable during a storage period of one year or more and less than four years;

[14] the Japanese encephalitis vaccine of [10], which further comprises an adjuvant;

[15] the vaccine of [14], wherein the amount of antigen per dose of the vaccine comprising the adjuvant is less than that of a vaccine without the adjuvant;

[16] the vaccine of any one of [10] to [15], which is in a liquid dosage form;

[17] a combination vaccine comprising the Japanese encephalitis vaccine of any one of [10] to [16], and another type of antigen;

[18] the combination vaccine of [17], wherein said another type of antigen is at least an antigen selected from diphtheria toxoid, tetanus toxoid, pertussis vaccine, *Haemophilus influenza* vaccine, *Neisseria meningitidis* vaccine, oral poliomyelitis vaccine, inactivated poliomyelitis vaccine, and hepatitis vaccine;

[19] a method for preventing a disease caused by a bacterium and/or virus in a subject, which comprises the step of administering the Japanese encephalitis vaccine of [10] or the combination vaccine of [17] to the subject; and

[20] the method of [19], wherein the disease is caused by the Japanese encephalitis virus.

Inactivated liquid Japanese encephalitis vaccines produced by the cell culture method are described below.

MODE FOR CARRYING OUT THE INVENTION

An objective of the present invention is to provide methods for producing effective and safe inactivated liquid Japanese encephalitis vaccines that can be stored for a long period even around room temperature, which comprise the step of combining multiple inactivation treatments for Japanese encephalitis viruses obtained by the cell culture method. Another objective of the present invention is to provide Japanese encephalitis vaccines produced by the production methods, and combination vaccines obtained by combining the stable Japanese encephalitis vaccines with other types of antigen vaccines. Another objective of the present invention is to provide uses of the vaccines.

Hereinbelow, "storage stability" means that the remaining titer of a Japanese encephalitis vaccine is retained during storage around room temperature. Unless otherwise specified, vaccines produced by the production methods of the present invention are liquid products. "Around room temperature" means a temperature within the range of 15 to 40° C. In the present invention, the storage period is preferably one year or more, more preferably two years or more and less than four years. As a matter of course, when produced as lyophilized products, the vaccines of the present invention can be stably stored in a cold place for a long period in a conventional manner.

Viral strains used to produce the Japanese encephalitis vaccines of the present invention may be any of clinically isolated strains, wild type strains, artificial mutant strains, attenuated live vaccine strains, and genetic recombinant strains, as long as they have antigenicity. The genetic recombinant strains include virus strains engineered by reverse genetics techniques. Meanwhile, both of the mouse brain method and the cell culture method may be used for obtaining viruses; however, the cell culture method is preferred.

Any cells may be used in cell culture for the viral strains, as long as the cells are susceptible to the Japanese encephalitis virus. Such cells include, for example, Vero cells, MDCK cells (non-adhesive cells), and Per.C6.

Media supplemented with serum are typically used in cell culture for Japanese encephalitis viruses to produce vaccines. However, from the safety viewpoint of vaccines, it is more preferable to use viruses obtained by serum-free culture. Unless otherwise specified, master and working cell banks used as seed for cell culture are commonly prepared by serum-supplemented culture. However, it is more preferable to use master and working cell banks prepared by serum-free culture. This can increase the safety of produced vaccines.

The cell culture method that was used herein by the present inventors to produce inactivated liquid Japanese encephalitis vaccines is outlined below.

Vero cells (ATCC CCL-81) purchased from ATCC were conditioned with serum-free medium, and master and working cell banks were prepared. Viruses of the Beijing-1 strain, which is a mouse brain-derived strain for use in producing Japanese encephalitis vaccine, were passaged over several generations using Vero cells to prepare master and working viral banks.

Vero cells were cultured on microcarriers (Cytodex-1 or -3; GE Healthcare) in serum-free medium for five to seven days. The Japanese encephalitis virus was inoculated when the cell density reached $1 \times 10^6$ cells/ml. After around three days of culture, the culture supernatant was collected to obtain a viral suspension.

After formalin inactivation, the viral suspension was purified by sucrose gradient centrifugation to prepare a vaccine. Stabilizers may be added at this time, i.e., after purification. The stabilizers include amino acids, amines, amides, and organic acids.

The inactivated liquid Japanese encephalitis vaccines of the present invention have markedly improved stability for long-term storage around room temperature. The methods for producing the improved inactivated Japanese encephalitis vaccines of the present invention are modified methods of conventional inactivation methods. The improvement in the present invention involves using either one or a combination of two types of the treatments described below for inactivation.

The first modification in the inactivation methods of the present invention is to carry out the inactivation in the presence of an amino acid or the like. In the present invention, the Japanese encephalitis virus is inactivated in a buffer containing an amino acid, amine, amide, or organic acid in addition to an inactivator (for example, formalin). This allows production of inactivated Japanese encephalitis vaccines that substantially retain their titers even during long-term storage around room temperature.

A method is known to control the degree of inactivation by having amino acids, ammonia, amines, or the like present when inactivating bacteria, whole virus, or protein toxins (see Non-Patent Document 6). For example, it has been commonly accepted that lysine reacts with formalin and traps excess formalin to neutralize its action, and thus lysine has the effect of controlling over progression of the inactivation or virtually terminating the inactivation. Furthermore, it has been proven that Shiff base is formed by reaction between formalin and the terminal amino group of lysine (see Non-Patent Documents 7 to 9).

Previously, it has been considered that thorough progression of inactivation, i.e., complete viral inactivation, is preferable for production of inactivated Japanese encephalitis vaccines. For this reason, amino acids, which have been considered to have the effect of inhibiting viral inactivation, are not added when inactivating Japanese encephalitis viruses with formalin. The present inventors varied the formalin concentration and duration of treatment in the production of inactivated vaccines, and assessed their correlation with the degree of inactivation. In this study, amino acid addition was performed as a method for controlling the inactivation. This showed an unexpected and novel effect of improving the storage stability. Thus, the present inventors successfully developed inactivated Japanese encephalitis vaccines that are stable even after long-term storage around room temperature.

It is a novel and useful finding by the present inventors that the presence of amino acids, amines, amides, or organic acids during inactivation of Japanese encephalitis vaccines has the effect of improving storage stability.

Any type of available amino acids can be used in the inactivation treatment of the present invention. Among them, protein-constituting amino acids are preferred. Furthermore, basic amino acids are more preferred. Water-soluble amino acids are often preferred; however, water-insoluble amino acids such as valine may be effective in some cases. It is possible to use both natural (L-type) and non-natural (D-type) amino acids. More preferred amino acids include, but are not limited to, aspartic acid, γ-aminobutyric acid, alanine, β-alanine, arginine, glycine, glutamic acid, isoleucine, leucine, lysine, serine, threonine, valine, and peptides, and amino acid oligomers containing thereof.

Preferred amines and amides include, but are not limited to, alkylamines such as ethylamine, ethanolamine, and propanolamine; amides such as urea, glycineamide, and β-alanylamide; ammonia; and inorganic salts of the above substances.

Acidic and basic amino acids, as well as amines can be used in the form of salt. Furthermore, simple amino acid esters such as methyl esters and ethyl esters can be used.

Preferred organic acids include, but are not limited to, succinic acid, tartaric acid, gluconic acid, oleic acid, lactobionic acid, and inorganic salts thereof. Furthermore, it is possible to use other pharmaceutically acceptable acids and salts thereof. Such acids and salts include, but are not limited to, for example, maleic acid, malic acid, stearic acid, linoleic acid, glucoheptonic acid, carboxyvinyl polymers, and inorganic salts thereof.

In the present invention, amino acids, amines, amides, or organic acids can be used practically at a concentration in the range of 0.005 to 0.5 M, preferably 0.02 to 0.2 M. However, the optimal concentration varies depending on the concentration of Japanese encephalitis virus, buffer pH, temperature of reaction solution for inactivation, etc. Methods for determining the optimal concentration are known to those skilled in the field of vaccines.

In the treatment, amino acids, amines, amides, or organic acids may be added at a time in the beginning, or added separately once or twice a week.

There is no particular limitation on the suitable Japanese encephalitis virus strains for producing Japanese encephalitis vaccines of the present invention. Specifically, it is possible to use any clinically isolated strains (i.e., wild type stains), artificial mutant strains, attenuated strains, genetic recombinant strains (including strains engineered by reverse genetics), as long as they can show antigenicity when used in producing vaccines.

The storage stability of the Japanese encephalitis virus vaccine products produced by the present invention can be assessed by determining the remaining titer during storage. Methods for determining the titer of Japanese encephalitis vaccines include immunoassay methods such as the neutralizing antibody titer method, HI method, and ELISA method. Of these methods, the neutralizing antibody titer method is preferred, since it has been adopted for the Minimum Requirements for Biological Products in Japan due to its simplicity and high reliability. The neutralizing antibody titer method is also referred to as "50% plaque-reduction method". In this method, samples of diluted immune antiserum are combined with a known amount of Japanese encephalitis virus solution; and the amount of remaining viruses is determined based on the number of plaques formed after contact with Vero cells; and the neutralizing antibody titer is defined as the degree of dilution that gives 50% plaque reduction. This method is known to those skilled in the field of vaccines.

The mechanism underlying the stabilizing effect produced by the presence of amino acids, amines, amides, or organic acids at the time of inactivation in the treatment methods of the present invention will be discussed below. The mechanism is explained using as an example an amino acid having a terminal amino group, such as glycine or lysine. Briefly, it is speculated that the conformation of polysaccharides and other structures on the viral surface is converted into a more stable conformation during inactivation in the presence of an amino acid, while formalin inactivation proceeds more thoroughly. Specifically, together with envelope proteins, large polysaccharide structures and other acidic macromolecules are tangled on the surface of Japanese encephalitis virus. Therefore, it is thought that some of the sites capable of reacting with formalin are covered on the viral surface. Thus, formalin molecules hardly reach some of the free amino groups of protein molecules on the viral surface.

In other words, in the conventional method in which inactivation is carried out in the absence of amino acids, formalin inactivates portions of proteins exposed on the viral surface, but it cannot inactivate the covered portions of proteins. Therefore, some of the viral proteins are thought to remain covered and thereby retain their activity. Such viruses are partially inactivated products.

According to the present invention, in the co-presence of an amino acid having a terminal amino group, such as glycine or lysine, the amino acid can bind to some portions of large viral structures because it has the property of forming a salt with an acidic substance. When an amino acid newly binds to some portions, polysaccharide molecules tangled on the viral surface undergo conformational changes, and previously covered amino groups are exposed as a result. Then, free formalin present nearby binds to the amino groups. It is speculated that the binding of formalin to viral surface proteins proceeds more thoroughly by the above process, and the conformation of proteins on the surface of inactivated viral particles becomes more stable. Alternatively, more complete formalin inactivation may result in enhanced resistance to the attack by a trace amount of proteases contaminated in vaccine products. The above is a possible explanation for the fact that Japanese encephalitis virus vaccines stably storable over a long period can be produced by formalin treatment in the presence of an amino acid or such.

The second modification in the inactivation methods of the present invention is a second viral inactivation treatment using physicochemical techniques. The second inactivation may be performed in the presence or absence of a chemical inactivator.

The conventional inactivation treatment of whole virus or proteins includes both chemical and physicochemical treatments. However, the inactivation has been performed using only one of chemical inactivation treatments with formalin or glutaraldehyde, and inactivation treatments using physicochemical techniques such as γ-ray or ultraviolet irradiation, and no combination of multiple inactivation methods has been carried out. It is understood that the inactivation is completed in the treatment for inactivating whole virus when viral inactivation is confirmed, or when the loss of functional activity is confirmed in the treatment for inactivating free proteins. Accordingly, combination of multiple inactivation treatments has been thought to be unnecessary, and thus there was no such attempt. The present inventors speculated that incomplete inactivation is a cause for the quality loss during storage of Japanese encephalitis virus vaccines produced by inactivation using chemical techniques. Thus, the present inventors investigated methods for inactivating Japanese encephalitis viruses. As a result, the present inventors discovered that performing a second inactivation by a physicochemical technique, in addition to a chemical inactivation treatment, is effective for increasing the storage stability of vaccines.

The second inactivation can be achieved by various physicochemical treatment methods. Such physicochemical methods include, but are not limited to the examples described below. Examples of possible conditions are also shown below; however, the conditions are not limited thereto.

<Physicochemical Treatments and Conditions>

Thermal treatment (temperature, 15 to 40° C.; duration of heating, 10 to 120 minutes); γ-ray irradiation (source, cobalt 60; 5 to 50 kGy (kilogray); laser irradiation (light source, various laser irradiators; wavelength, 500 to 700 nm; amount of light, 0.01 to 1 J (joule)/cm$^2$); electron beam irradiation (microwave); sonication.

Furthermore, quality loss can be prevented by microencapsulation of whole virus. It is possible to use one or more of the above methods in combination. The same method may be repeated several times. The treatment conditions are not necessarily constant, and appropriate conditions can be determined by varying the amount of suspended virus, temperature, buffer pH, duration of treatment, etc. The above physicochemical treatments are carried out under sterile conditions.

In the first and second inactivations, the treatments may result in excessive denaturation of antigen proteins and loss of antigenicity under certain treatment conditions. Thus, from a comprehensive standpoint, optimal methods and treatment conditions should be selected by examining the immunogenicity and other properties after treatment.

In the second inactivation of the present invention, at least a physicochemical inactivation treatment is carried out. When the inactivation is performed by using multiple treatments in combination, a chemical inactivation treatment may be followed by a physicochemical inactivation treatment, or a physicochemical inactivation treatment may be followed by a chemical inactivation treatment.

The mechanism underlying the effect of the second inactivation of the present invention is discussed below using thermal inactivation as an example. A mechanism similar to formalin inactivation in the presence of an amino acid can be hypothesized. Briefly, in the case of formalin inactivation using a mild physicochemical treatment, for example, mild thermal treatment, it is speculated that polysaccharides and other structures on the viral surface undergo conformational changes, and the binding of formalin to the viral surface proceeds more completely, thus enhancing the stability. The combination of a chemical inactivation treatment in the presence of an amino acid and a second inactivation treatment using a physicochemical technique includes, for example, formalin inactivation in the presence of an amino acid with mild heating.

As a supporting fact for the above mechanism, all treatments with confirmed effectiveness, such as thermal treatment, γ-ray irradiation, and sonication, share the effect of inducing conformational changes in polymer structures such as polysaccharides and conjugated proteins under mild conditions.

The above methods for producing stable Japanese encephalitis vaccines can be also applied to the production of whole-virus vaccines derived from other viruses belonging to Flaviviridae. Such Flaviviridae viruses include dengue virus, yellow fever virus, tick-borne encephalitis virus (TBE), West Nile fever virus, and Saint Louis encephalitis virus. The methods are also used to produce whole influenza virus vaccines.

The stable Japanese encephalitis vaccines of the present invention can be used to produce combination vaccines in which other types of antigen vaccines are combined. For example, a Japanese encephalitis vaccine of the present invention may be combined with a DTP three-way vaccine which is a mixture of tetanus toxoid, diphtheria toxoid, and pertussis vaccine, and this combination vaccine can be used as a four-way vaccine. Other bacterial vaccine antigens include *Haemophilus influenza* type B, *Neisseria meningitidis, Salmonella typhi*, enterotoxigenic *Escherichia coli, Vibrio cholera, Staphylococcus aureus*, and *Streptococcus pneumoniae*. Meanwhile, viral antigens include, but are not limited to, oral poliomyelitis vaccines, inactivated poliomyelitis vaccines, hepatitis vaccines, and influenza vaccines.

Addition of effective adjuvants to vaccines is known to enhance the vaccination effect. Accordingly, appropriate adjuvants can also be added to the vaccines of the present invention, including combination vaccines. Adjuvants applicable to the vaccines of the present invention include, but are not limited to aluminium hydroxide and inorganic salts thereof, hydrocarbons such as squalene and oils, bacterial toxins such as cholera toxin, and polysaccharides such as inulin, and combinations thereof. In general, there is no established rule on the type of effective adjuvant for enhancing the immunological action of a certain vaccine antigen. The type of effective adjuvant also varies depending on the administration method. However, those skilled in the art can determine the type and concentration of effective adjuvant for a vaccine by known trial-and-error methods.

As with other conventional vaccines, the vaccine products of the present invention may contain in addition to antigens, stabilizers (for example, gelatin), preservatives (for example, thimerosal and phenoxy ethanol), and coloring agents (for example, phenol red).

The present invention also relates to methods for preventing a disease caused by bacteria and/or viruses in a subject, which comprise the step of administering a vaccine of the present invention to the subject. Herein, the disease includes those caused by Japanese encephalitis viruses.

Herein, "administration" includes both oral and parenteral administration. Oral administration includes administration of oral agents. The dosage form of oral agents can be selected from tablets, capsules, solutions, suspensions, etc. Transnasal and transdermal administration are also possible if appropriate dosage forms are selected.

Parenteral administration includes administration by injection.

The dosage and administration method vary depending on the body weight, age, and symptom of a subject, and can be appropriately selected by those skilled in the art.

Hereinbelow, the present invention is described with reference to the Examples; however, it should not be construed as being limited thereto.

All prior-art documents cited herein are incorporated into this specification by reference.

EXAMPLES

Example 1

Effect on the Storage Stability of Vaccines by Amino Acids Added at the Time of Inactivation Improved Japanese encephalitis virus vaccines were obtained by inactivating the virus with formalin in the presence of an amino acid. The vaccines were stored and assessed for their storage stability. The method employed is described below.

The Beijing-1 Japanese encephalitis virus strain was used. The culture medium used was a serum-free cell culture medium, VP-SFM (Invitrogen). Cell culture was carried out using an 80-l fermenter containing 50 l of medium.

Vero cells (ATCC CCL-81) purchased from ATCC were conditioned in serum-free medium to prepare master and working cell banks. Viruses of the Beijing-1 strain, which is a mouse brain-derived strain for use in producing Japanese encephalitis vaccines, were passaged over several generations using Vero cells to prepare master and working viral banks.

Vero cells were cultured on microcarriers (Cytodex-1 or -3) in a serum-free medium for five to seven days. The Japanese encephalitis virus was inoculated when the cell density reached $1\times10^6$ cells/ml. After about three days of culture, the virus was collected from the culture supernatant, and purified using the method for producing Japanese encephalitis virus vaccines by Kitasato Institute. Then, the virus was suspended in phosphate-buffered saline (PBS) to prepare a viral suspension.

Then, the virus was inactivated by 4° C. incubation for three months in the presence of 0.05% (v/v) formalin. In this treatment, one or more amino acids at 0.5% and other test substances were added to the viral suspension (Table 1).

After the inactivation treatment, impurities, formalin, and additives were removed by sucrose density gradient centrifugation, and the viral concentration was adjusted with PBS. Then, the solutions were aliquoted (0.7 ml) into vials to prepare Japanese encephalitis vaccines.

Each vial was stored in a cold place at 4° C. The vials were opened every three months from the start of storage up to nine months. Five vials of samples prepared under the same conditions were combined into a single sample. Five samples were used to assay the remaining titer after each storage period by the titer assay method according to the Minimum Requirements for Biological Products in Japan. The remaining titer after each storage period is presented as the neutralizing antibody titer in Table 1.

Example 2

Effect of Added Amino Acid on Long-Term Storage of Liquid Japanese Encephalitis Vaccine Products Viral suspensions were prepared by the same method described in Example 1. Using these suspensions, the Japanese encephalitis virus was inactivated with formalin in the presence or absence of 0.5% glycine. To remove impurities, the virus was then purified by sucrose density gradient centrifugation. The virus was resuspended in PBS at a viral protein concentration of 10 μg/ml. The suspensions were aliquoted (0.7 ml) into vials and used as vaccines. At this time, an amino acid and a sugar alcohol were added as stabilizers to the vaccines in the vials. The vials were stored at 4° C. or 28° C. to assess the storage stability. Specifically, the remaining titer in each vial was assayed every three months by the method indicated in the Minimum Requirements for Biological Products. The result is shown in Table 2. The titer is presented as the neutralizing antibody titer.

The result shown in Table 2 demonstrates the following:
1. Comparisons between Assay Nos. 1 and 3 and between Assay Nos. 2 and 4 show that after 15 months of storage, the liquid Japanese encephalitis vaccine products produced by viral inactivation in the presence of an amino acid exhibited a higher titer, as compared to the products inactivated without amino acid addition. That is, amino acid addition in the inactivation treatment is an effective method for producing stable Japanese encephalitis vaccines.
2. Comparison between Assay Nos. 3 and 4 shows that after 15 months of storage, the remaining titer was higher when amino acid and sugar alcohol were added as stabilizers to the vaccine as compared to when no additive was added. Meanwhile, comparison between Assay Nos. 1 and 2 shows that the Japanese encephalitis vaccines of the present invention inactivated with formalin in the presence of an amino acid had sufficient stability, and additional stabilizing effect of the amino acid and sugar alcohol was unclear after 12 months of storage. After 15 months of storage, the remaining titer was higher in Assay No. 1.
3. The remaining titer was higher both after storage at 4° C. and 28° C. in Assay No. 1, as compared to the control without additives (Assay No. 3). The difference was clearer when stored at 28° C. The same was observed for Assay No. 2.
4. It was revealed that the remaining titer was higher after 4 months of storage at 28° C. in Assay No. 1, as compared to the control without additives (Assay No. 3). That is, it was demonstrated that amino acid addition in the inactivation treatment is an effective method for producing stable Japanese encephalitis vaccines.

TABLE 1

| Assay No. | Amino acid and sugar alcohol added at the time of inactivation | | Storage temperature | Neutralizing antibody titer of stored vaccine 10E(n) | | | |
|---|---|---|---|---|---|---|---|
| | | | | 0 month | 3 months | 6 months | 9 months |
| 1 | 0.5% Glycine | | 4° C. | 2.264 | 2.550 | 2.501 | 2.101 |
| 2 | 0.5% Glycine | 1.8% Sorbitol | 4° C. | 2.661 | 2.536 | 2.469 | 2.060 |
| 3 | 0.4% L-Glutamine | 1.8% Sorbitol + 5% Lactose | 4° C. | 2.653 | 2.401 | 2.116 | 1.563 |
| 4 | 0.5% Glycine + 0.4% L-Glutamine | 1.8% Sorbitol + 5% Lactose | 4° C. | 1.890 | 2.506 | 2.227 | 1.476 |
| 5 | No additive (control) | | 4° C. | 2.639 | 1.759 | 0.907 | 0.299 |

As shown in Table 1, the results of 6- and 9-month storage demonstrate that the remaining titer of the Japanese encephalitis vaccine products to which amino acids such as glycine and glutamine (Assay Nos. 1 to 4), or amino acids and sugar alcohols (Assay Nos. 2 to 4) were added at the time of formalin inactivation treatment of the Japanese encephalitis virus, was higher than the remaining titer of products inactivated by the conventional method in the absence of additives (Assay No. 5). That is, it was revealed that the long-term storage stability was enhanced when the inactivation treatment was performed in the presence of the above additives as compared to in the absence of the additives. The titer was drastically decreased in the product inactivated by the conventional method without addition of amino acid or sugar alcohol (control).

TABLE 2

| Stabilizer | | Storage | Neutralizing antibody titer of stored vaccine 10E(n) | | | | | |
|---|---|---|---|---|---|---|---|---|
| During inactivation | After purification | temperature | 0 month | 3 months | 6 months | 12 months | 15 months | 24 months |
| 1 0.5% Glycine | No additive | 4° C. | 2.017 | 2.475 | 2.347 | 2.714 | 2.324 | 2.533 |
| | | 28° C. | 2.017 | 2.906 | 1.767 | 2.537 | 3.127 | 2.630 |
| 2 0.5% Glycine | 0.5% Glycine | 4° C. | 2.373 | 2.132 | 2.186 | 2.874 | 2.042 | 2.630 |
| | 1% Sorbitol | 28° C. | 2.373 | 2.579 | 2.616 | 2.695 | 2.345 | 1.523 |
| 3 No additive | No additive | 4° C. | 2.298 | 1.350 | 1.350 | 1.542 | 1.859 | 1.271 |
| | | 28° C. | 2.298 | 1.498 | 1.498 | 2.023 | 1.694 | 1.465 |
| 4 No additive | 0.5% Glycine | 4° C. | 1.755 | 2.557 | 1.788 | 1.767 | 2.024 | 2.436 |
| | 1% Sorbitol | 28° C. | 1.755 | 1.942 | 1.530 | 2.274 | 2.580 | 1.659 |

Example 3

Protective Effect of the Vaccines Against Infection after Two Years of Storage

As described in Example 1, viral suspensions were prepared by culturing cells in serum-free medium. As described in Example 2, the viral suspensions were treated with formalin for inactivation at 4° C. for three months in the presence of 0.5% glycine, and purified by sucrose density gradient centrifugation to remove impurities. Then, the suspensions were aliquoted (0.7 ml) into vials and used as vaccines. The vaccines were stored at 4° C. or 28° C. for 25 months. To assess the efficacy of the stored vaccines, mice immunized with them were infected with the virus, and the protective effect against infection was evaluated. ddY mice (4 weeks old) were immunized with the stored vaccines four times at three-day intervals. After two weeks, 0.03 ml of a Japanese encephalitis virus solution (50 $LD_{50}$) was intracerebrally inoculated into the mice, and then they were observed for two weeks to assess their survival. The number of survived mice and survival rate are shown in Table 3. A cell culture-derived vaccine produced by inactivation treatment without adding any vaccine stabilizer was used as a control. Furthermore, a mouse brain-derived vaccine used in the national assay (lyophilized product; purchased from the National Institute of Infectious Diseases) was dissolved in PBS in a prescribed fashion upon each measurement, and employed as a standard vaccine for titer determination (reference vaccine).

As seen in Assay No. 1 of Table 3, the mouse survival rate after viral infection was 83% after 25-month storage at 28° C. when the vaccine product was inactivated in the presence of 0.5% glycine but does not contain the amino acid after purification or in the product (Assay No. 1; "28° C."). Meanwhile, the survival rate was 80% when the reference vaccine was used and treated in the same manner (Assay No. 4). The above result demonstrates that the vaccines of the present invention can be stably stored in a liquid form at 28° C. for two years or more.

The survival rate was 67% when the vaccine was stored at 4° C. (Assay No. 1; "4° C.").

It was demonstrated that when the inactivation treatment was carried out in the presence of an amino acid, and the amino acid and sugar alcohol were added to the vaccine as preservatives during storage, the remaining efficacy of the vaccine (Assay No. 2) was lower than that in Assay No. 1, but higher than that of the control without additives (Assay No. 3). The conventional product could not be stably stored due to significant titer loss.

TABLE 3

| | Substance added | | | Mouse survival rate (%) after viral infection | | | | |
|---|---|---|---|---|---|---|---|---|
| Assay No. | During inactivation | In vaccine | Storage temperature | Number of mice | Day 6 | Day 8 | Day 10 | Day 14 |
| 1 | 0.5% Glycine | No additive | 4° C. | 6 | 100 | 67 | 67 | 67 |
| | | | 28° C. | 6 | 100 | 83 | 83 | 83 |
| 2 | 0.5% Glycine | 1% Sorbitol 0.5% Glycine | 4° C. | 10 | 100 | 50 | 40 | 40 |
| | | | 28° C. | 10 | 100 | 50 | 30 | 30 |
| 3 | No additive (control) | No additive (control) | 4° C. | 10 | 100 | 20 | 10 | 10 |
| | | | 28° C. | 10 | 100 | 40 | 20 | 20 |
| 4 | Reference vaccine (lyophilized product) | | | 10 | 100 | 90 | 80 | 80 |

Example 4

Effect of Amino Acid Added after Purification on the Storage Stability of the Vaccine Viral suspensions were prepared by the same method described in Example 1. The Japanese encephalitis virus was inactivated by adding formalin to the suspensions in the presence of 0.5% glycine and 1% sorbitol. Then, the virus was purified by sucrose density gradient centrifugation to remove impurities. After centrifugation, the virus was resuspended in PBS at a viral protein concentration of 10 µg/ml, and this was used as a vaccine. Together with 1% sorbitol, various amino acids were added as stabilizers to the suspensions, and they were stored. The remaining titers were determined every three months up to six months, as described in Example 2. The result is shown in Table 4.

TABLE 4

| | Stabilizer | | Storage | Neutralizing antibody titer of stored vaccine 10E(n) | | |
|---|---|---|---|---|---|---|
| | During inactivation | After purification | temperature | 0 month | 3 months | 6 months |
| 1 | 0.5% Glycine | | 4° C. | 2.175 | 3.303 | 2.128 |
| | | 1% Sorbitol | 28° C. | 2.175 | 2.736 | 2.651 |
| 2 | 0.5% Lysine | | 4° C. | 2.175 | 2.433 | 2.646 |
| | | 1% Sorbitol | 28° C. | 2.175 | 3.082 | 2.305 |
| 3 | 0.5% Alanine | | 4° C. | 2.175 | 2.235 | 2.032 |
| | | 1% Sorbitol | 28° C. | 2.175 | 3.198 | 3.058 |
| 4 | 0.5% Arginine | | 4° C. | 2.175 | 2.724 | 2.289 |
| | | 1% Sorbitol | 28° C. | 2.175 | 2.977 | 3.058 |
| 5 | 0.5% Valine | | 4° C. | 2.175 | 2.118 | 2.730 |
| | | 1% Sorbitol | 28° C. | 2.175 | 2.017 | 2.468 |
| 6 | | 1% Sorbitol | 4° C. | 2.175 | 2.445 | 2.718 |
| | | | 28° C. | 2.175 | 1.913 | 1.734 |
| 7 | | No additive | 4° C. | 2.175 | 2.468 | 2.629 |
| | | | 28° C. | 2.175 | 2.631 | 2.333 |

The result shown in Table 4 demonstrates the following:

The titer obtained by addition of glycine (Assay No. 1), alanine (Assay No. 2), or arginine (Assay No. 4) was higher than the titer obtained without additives (Assay No. 7; "28° C."). It was thus demonstrated that amino acid addition after purification, in combination with amino acid addition at the time of inactivation, retains the stability of Japanese encephalitis vaccines during storage at 28° C.

Example 5

Combination Vaccine of DTP Three-Way Vaccine and Improved Japanese Encephalitis Vaccine Viral suspensions were obtained by inactivation treatment as described in Example 2. The virus was inactivated by incubating the suspensions with formalin at 24° C. for ten days in the presence of 0.5% glycine, and this was used as a Japanese encephalitis vaccine. Meanwhile, a combination vaccine was prepared by combining equal amounts of a DTP three-way vaccine from Kitasato Institute and the stable Japanese encephalitis vaccine of the present invention.

The titer of each antigen component was determined by the method indicated in the Minimum Requirements for Biological Products in Japan. The result is shown in Table 5. All the items tested in the titer tests conformed to the Minimum Requirements for Biological Products in Japan.

TABLE 5

| | Test item | The Minimum Requirements for Biological Products in Japan | Measured value | Assessment |
|---|---|---|---|---|
| Toxicity test | Abnormal toxicity test | No abnormality | No abnormality | Conformed |
| | Mouse histamine sensitization test | 0.4 unit or less | 0.08 unit | Conformed |
| | Diphtheria toxin inactivation test | No abnormality | No abnormality | Conformed |
| | Tetanus toxin inactivation test | No abnormality | No abnormality | Conformed |
| Titer test | Japanese encephalitis vaccine | 8 units or more | 42 units | Conformed |
| | Diphtheria toxoid | 47 units or more | 100 units | Conformed |
| | Tetanus toxoid | 27 units or more | 32 units | Conformed |

INDUSTRIAL APPLICABILITY

The efficacy of the Japanese encephalitis vaccines produced by the production methods of the present invention is comparable with or higher than that of inactivated liquid Japanese encephalitis vaccines produced by the conventional mouse brain method. Furthermore, the vaccines of the present invention have improved safety and storage stability than the conventional vaccine products.

As for safety, the risk of contamination of vaccines with serum-derived adventitious agents, for example, BSE (mad cow disease) agents or hepatitis viruses is low because prior to the inactivation step, a master cell bank prepared by the serum-free culture method is used as a seed for cell culture and the virus is prepared by culture using the serum-free cell culture method. Thus, the Japanese encephalitis vaccines produced by the production methods of the present invention are safer than conventional vaccine products and Japanese encephalitis vaccines produced by the cell culture method using serum supplements.

It is important and beneficial that the vaccine titer is stably retained over long-term storage. In particular, liquid products that can be stored for a long period even around room temperature are very convenient from the viewpoint of production management, product distribution, and storage for clinical practice. In the case of the Japanese encephalitis virus which spreads in the semitropical and tropical regions for a long period, it is necessary to store various types of vaccines for a long period by simple temperature management in order to prevent infection using the vaccines. The vaccines of the present invention are useful when long-term storage is needed.

The invention claimed is:

1. A method for producing an inactivated whole Japanese encephalitis vaccine, comprising:
   (1) producing a Japanese encephalitis virus in cell culture;
   (2) inactivating the Japanese encephalitis virus by the following step(s) of (a) or (a) and (b):

(a) adding (i) an inactivator and (ii) an amino acid, amine, amide, organic acid, or combination thereof to the Japanese encephalitis virus to carry out a chemical inactivation treatment; and/or
(b) carrying out a physicochemical inactivation treatment for the Japanese encephalitis virus;
(3) purifying the inactivated virus to remove (i) and (ii) as set forth in (a); and
(4) storing the inactivated virus at a temperature between 15° C. and 40° C. for one year or more in the absence of an amino acid, wherein the inactivated virus is stored less than four years.

2. The method for producing a Japanese encephalitis vaccine of claim 1, wherein the inactivation is a chemical inactivation as set forth in (a) and an amino acid is added to the Japanese encephalitis virus, wherein the amino acid is selected from the group consisting of aspartic acid, γ-aminobutyric acid, alanine, β-alanine, arginine, glycine, glutamic acid, isoleucine, leucine, lysine, serine, threonine, and valine.

3. The method for producing a Japanese encephalitis vaccine of claim 1, wherein the inactivation is a chemical inactivation as set forth in (a) and an amine is added to the Japanese encephalitis virus, wherein the amine is selected from the group consisting of ethylamine, ethanolamine, propanolamine, and combination thereof.

4. The method for producing a Japanese encephalitis vaccine of claim 1, wherein the inactivation is carried out by a chemical inactivation as set forth in (a) and a physicochemical inactivation as set forth in (b) and the physicochemical inactivation is selected from the group consisting of heating, γ-ray irradiation, electron beam irradiation, and laser irradiation.

5. The method for producing a Japanese encephalitis vaccine of claim 4, wherein the physicochemical inactivation treatment by heating is carried out at 24° C. or higher.

6. The method for producing a Japanese encephalitis vaccine of claim 1, wherein the Japanese encephalitis virus is selected from the group consisting of a clinically isolated strain (wild type strain), an artificial mutant strain, a genetic recombinant strain, and a strain engineered by reverse genetics.

7. The method for producing a Japanese encephalitis vaccine of claim 1, wherein the cell culture is serum-free culture.

8. The method for producing a Japanese encephalitis vaccine of claim 7, further comprising preparing a master cell bank that serves as a seed for cell culture.

9. The method for producing a Japanese encephalitis vaccine of claim 1, wherein the inactivation is a chemical inactivation as set forth in (a) and an amide is added to the Japanese encephalitis virus, wherein the amide in (a) is selected from the group consisting of urea, glycineamide, β-alanylamide, and combination thereof.

10. The method for producing a Japanese encephalitis vaccine of claim 1, wherein the inactivation is a chemical inactivation as set forth in (a) and an organic is added to the Japanese encephalitis virus, wherein the organic acid in (a) is selected from the group consisting of succinic acid, tartaric acid, gluconic acid, oleic acid, lactobionic acid, and combination thereof.

* * * * *

UNITED STATES PATENT AND TRADEMARK OFFICE
CERTIFICATE OF CORRECTION

PATENT NO. : 9,453,055 B2  
APPLICATION NO. : 12/810447  
DATED : September 27, 2016  
INVENTOR(S) : Tomoyoshi Komiya and Hiroko Toriniwa Page 1 of 1

It is certified that error appears in the above-identified patent and that said Letters Patent is hereby corrected as shown below:

On the Title Page

(73) Assignee:

"Tokyo" should be replaced by "Saitama".

Signed and Sealed this  
Twenty-first Day of February, 2017

Michelle K. Lee  
*Director of the United States Patent and Trademark Office*